(12) United States Patent
Ashkar

(10) Patent No.: US 6,686,444 B2
(45) Date of Patent: *Feb. 3, 2004

(54) OSTEOPONTIN DERIVED CHEMOTACTIC PEPTIDES AND METHODS OF USE

(75) Inventor: Samy Ashkar, Boston, MA (US)

(73) Assignee: Children's Medical Center Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 123 days.

This patent is subject to a terminal disclaimer.

(21) Appl. No.: 08/918,189

(22) Filed: Aug. 21, 1997

(65) Prior Publication Data

US 2002/0192208 A1 Dec. 19, 2002

Related U.S. Application Data

(60) Provisional application No. 60/023,427, filed on Aug. 22, 1996.

(51) Int. Cl.⁷ ................................................. C07K 7/00
(52) U.S. Cl. ........................ 530/329; 530/324; 530/325; 530/326; 530/327; 530/328; 514/12; 514/13; 514/14; 514/15; 514/16; 514/17
(58) Field of Search ............................. 514/2, 16, 12, 514/13, 14, 15, 17; 530/329, 324, 325, 326, 327, 328

(56) References Cited

U.S. PATENT DOCUMENTS

| | | | |
|---|---|---|---|
| 4,693,718 A | 9/1987 | Urry et al. | 623/11 |
| 4,976,734 A | * 12/1990 | Urry | 623/11 |
| 5,519,003 A | * 5/1996 | Mochly-Rosen | 514/16 |
| 5,773,569 A | * 6/1998 | Wrighton | 530/300 |
| 5,989,553 A | * 11/1999 | Johnston | 424/190.1 |

FOREIGN PATENT DOCUMENTS

EP 0269595 1/1988

OTHER PUBLICATIONS

Liaw, Circulation Research 74, 214, 1994.*
Yue, Exp. Cell Res. 214, 459, 1994.*
Yamamoto, Ann NY Acad Sci 760, 378, 1995.*
Lombardi, et al. "Neutralizing antibodies directed against osteopontin inhibit FMLP induced macrophage infiltration in rat skin" *FASEB Journal*, (1996); 10(6):a1293, abstr. 1694.
Nasu, et al. "Expression of wild–type and mutated rabbit osteopontin in *Escherichia coli*, and their effects on adhesion and migration of P388D1 cells" *Biochem. Journal*, (1995); 307:257–65.
Ullrich, et al. "Biosynthesis and secretion of an osteopontin–related 20kDa polypeptide in the Madin–Darby canine kidney cell line" *Journal of Biological Chemistry*, (1991); 266(6):3518–25.
Van Dijk, et al. "Evidence that a non–RGD domain in rat osteopontin is involved in cell attachment" *Journal of Bone and Mineral Research*, (1993); 8(12): 1499–1506.
Xuan, et al. "Site–directed mutagenesis of the RGD sequence in osteopontin destroys cell adhesion and migration functions" *Journal of Cellular Biochemistry*, (1995); 57: 680–90.
Patarca, R. et al., "Differential Induction of Interferon γ Gene Expression After Activation of CD4+ T Cells by Conventional Antigen and M1s Superantigen," *PNAS USA*, vol. 88, 2736–9 (1991).
Patarca, R. et al., "Dysregulated Expression of the T Cell Cytokine Eta–1 in CD4–8– Lymphocytes During the Development of Murine Autoimmune Disease," *J. Exp. Med.*, vol. 172, 1177–83 (1990).
Patarca, R. et al., "Molecular and Cellular Basis of Genetic Resistance to Bacterial Infection: The Role of the Early T–lymphocyte Activation–1/Osteopontin Gene," *Critical Reviews in Immunology*, vol. 13, Nos. 3–4, 225–46 (1993).
Patarca, R. et al., "Structural and Functional Studies of the Early T Lymphocyte Activation 1 (Eta–1) Gene," *The Journal of Experimental Medicine*, vol. 170, 145–61 (1989).
Pettersson, E. et al., "Synthesis, NMR and Function of an O–Phosphorylated Peptide, Comprising the RGD–Adhesion Sequence of Osteopontin," *Acta Chemica Scandinavica*, vol. 45, 604–8 (1991).
Rodan, G., "Osteopontin Overview," *Annals New York Academy of Sciences*, 1–5 (1995).
Seiter, S. et al., "Prevention of Tumor Metastasis Formation by Anti–Variant CD44," *J. Exp. Med.*, vol. 177, 443–55 (1993).
Senger, D. et al., "Adhesive Properties of Osteopontin: Regulation by a Naturally Occurring Thrombin–Cleavage in Close Proximity to the GRGDS Cell–binding Domain," *Molecular Biology of the Cell*, vol. 5, 565–74 (1994).
Senger, D. et al., "Elevated Expression of Secreted Phosphoprotein I (Osteopontin, 2ar) as a Consequence of Neoplastic Transformation," *Anticancer Research*, vol. 9, 1291–1299 (1989).
Singh, R. et al., "Definition of a Specific Interaction Between the Early T Lymphocyte Activation 1 (Eta–1) Protein and Murine Macrophages in Vitro and its Effect upon Macrophages in Vivo," *J. Exp. Med.*, vol. 171, 1931–42 (1990).

(List continued on next page.)

*Primary Examiner*—Christopher S. F. Low
*Assistant Examiner*—David Lukton
(74) *Attorney, Agent, or Firm*—Holland & Knight LLP

(57) ABSTRACT

Novel osteopontin derived chemotactic peptides are described. The peptides (or antagonists thereof) are useful in treating conditions or diseases associated with chemotaxis.

15 Claims, No Drawings

OTHER PUBLICATIONS

Smith, J. and Denhardt, D., "Molecular Cloning of a Tumor Promoter–Inducible mRNA Found in JB6 Mouse Epidermal Cells: Induction is Stable at High, but not at Low, Cell Densities," *Journal of Cellular Biochemistry*, vol. 34, 13–22 (1987).

Sørensen, E. and Petersen, T., "Identification of Two Phosphorylation Motifs in Bovine Osteopontin," *Biochemical and Biophysical Research Communications*, vol. 198, No. 1, 200–5 (1994).

Sørensen, E. et al., "Posttranslational Modifications of Bovine Osteopontin: Identification of Twenty–Eight Phosphorylation and Three O–glycosylation Sites," *Protein Sci.*, vol. 4, No. 10, 2040–9 (1995).

Van Dijk, S. et al., "Evidence that a Non–RGD Domain in Rat Osteopontin is Involved in Cell Attachment," *Journal of Bone and Mineral Research*, vol. 8, No. 12, 1499–1506 (1993).

Weber, G. et al., "Receptor–Ligand Interaction Between CD44 and Osteopontin (Eta–1)," *Science*, vol. 271, 509–12 (1996).

Young, M. et al., "cDNA Cloning, mRNA Distribution and Heterogeneity, Chromosomal Location, and RFLP Analysis of Human Osteopontin (OPN)," *Genomics*, vol. 7, 491–502 (1990).

Behrend, E., et al., "Reduced Malignancy of ras–transformed NIH 3T3 Cells Expressing Antisense Osteopontin RNA," *Cancer Research*, vol. 54, 832–7 (1994).

Chambers, A. et al., "Induction of Expression of Osteopontin (OPN; Secreted Phosphoprotein) in Metastatic, Ras–Transformed NIH 3T3 Cells," *Anticancer Research*, vol. 12, 43–7 (1992).

Craig, A. et al., "Secreted Phosphoprotein mRNA is Induced During Multi–Stage Carcinogenesis in Mouse Skin and Correlates with the Metastatic Potential of Murine Fibroblasts," *Int. J. Cancer*, vol. 46, 133–7 (1990).

Denhardt, D. and Guo, X., "Osteopontin: a Protein with Diverse Functions," *FASEB J.*, vol. 7, 1475–82 (1993).

Folkman, J., "What is the Role of Endothelial Cells in Angiogenesis?" *Laboratory Investigation*, vol. 51, No. 6, 601–604 (1984).

Giachelli, C. et al., "Molecular Cloning and Characterization of 2B7, a Rat mRNA which Distinguishes Smooth Muscle Cell Phenotypes in Vitro and is Identical to Osteopontin (Secreted Phosphoprotein I, 2aR)," *Biochemical and Biophysical Research Communications*, vol. 177, No. 2, 867–73 (1991).

Günthert, U., et al., "A New Variant of Glycoprotein CD44 Confers Metastatic Potential to Rat Carcinoma Cells," *Cell*, vol. 65, 13–24 (1991).

Kiefer, M. et al., "The cDNA and Derived Amino Acid Sequence for Human Osteopontin," *Nucleic Acids Research*, vol. 17, No. 8, 3306 (1989).

Kubota, T. et al., "Multiple Forms of SPPI (Secreted Phosphoprotein, Osteopontin) Synthesized by Normal and Transformed Rat Bone Cell Populations: Regulation by TGF–β," *Biochemical and Biophysical Research Communications*, vol. 162, No. 3, 1453–9 (1989).

Lampe, M. et al., "Polyclonal B Cell Activation by the Eta–1 Cytokine and the Development of Systemic Autoimmune Disease," *The Journal of Immunology*, vol. 147, No. 9, 2902–6 (1991).

Oldberg, A. et al., "Cloning and Sequence Analysis of Rat Bone Sialoprotein (Osteopontin) cDNA Reveals an Arg–Gly–Asp Cell–binding Sequence," *PNAS USA*, vol. 83, 8819–23 (1986).

Oldberg, A. et al., "Identification of a Bone Sialoprotein Receptor in Osteosarcoma Cells," *The Journal of Biological Chemistry*, vol. 263, No. 36, 19433–6 (1988).

* cited by examiner

OSTEOPONTIN DERIVED CHEMOTACTIC PEPTIDES AND METHODS OF USE

This application claims the benefit of a previously filed Provisional Application No. 60/023,427, filed Aug. 22, 1996, which is hereby incorporated by reference.

This invention was made with government support from the National Institutes of Health. Accordingly, the government has certain rights in the invention.

BACKGROUND OF THE INVENTION

The formation of metastases from a primary tumor is a complex temporal process that involves angiogenesis, invasion of the circulatory system by tumor cells, intravasation of the endothelium, arrest in the venous or capillary bed of the target organ, extravasation, entry into the target parenchyme and proliferation of the secondary tumor in tissue different from its tissue of origin. Throughout this process metastatic tumor cells are constantly interacting with their host tissue modulating their adhesiveness to cells and extracellular matrices, degrading matrices and migrating into interstitial stroma. These events are not unique to tumor metastasis and occur in other processes such as angiogenesis, tissue remodeling, bone remodeling and embryogenesis. Experimental studies have demonstrated that invasion involves the active locomotion of tumor cells through and into tissue barriers. The molecular mechanisms regulating such invasive tumor cell migration and subsequent implantation are poorly understood but it appears that there is organ specificity of colonization.

Several substances that stimulate tumor cell locomotion in vitro have been described. These include factors derived from resorbing bone, liver and smooth muscle. Locomotion of tumor cells can also be induced by endogenous substances in an autocrine fashion. These factors can induce two types of directed cell locomotion: (1) chemotaxis, i.e., directed locomotion of cells up a soluble gradient; or (2) haptotaxis, i.e., migration of cells up a gradient of attached molecules.

Bone metastases are frequently one of the first signs of disseminated disease in certain carcinomas of lung, breast, prostate, kidney or thyroid. Osteoblasts, the bone forming cells, have been shown to secrete substances that induce the chemotaxis and invasion of melanoma and breast cancer cells. One product of osteoblasts that induces the migration of several cell types and is secreted by several tumors is osteopontin.

Osteopontin (Oldberg et al. (1986) *Proc. Natl. Acad. Sci. USA* 83:8819; Oldberg et al. (1986) *J. Biol. Chem.* 263:19433–19436) also known as OPN (Wrana et al. (1989) *Nucl. Acid Res.* 17:3306), 2ar (Smith, J. H. and Denhardt, D. T. (1987). *J. Cell Biochem.* 34: 10–22), transformation-associated secreted phosphoprotein (Senger et al. (1989) *Anticancer Res.* 48:1291), or Early T-lymphocyte activation-1 (Patarca et al. (1991) *Proc. Natl. Acad, Sci. USA* 88:2736), is a secreted glycosylated phosphoprotein expressed by bone (Oldberg et al. (1986) *J. Biol. Chem.* 263: 19433–19436), activated T-lymphocytes (Patarca et al. (1989) *J. Exp. Med.* 170:145–161; Patarca et al. (1991) *Proc. Natl. Acad. Sci. USA* 88:2736), macrophages (Singh et al. (1990). *J. Exp. Med* 171:1931–1942), smooth muscle cells of the vascular system (Giachelli et al. (1991) *Biochem. Biophys. Res. Commun.* 177: 867–873), and carcinomas and sarcomas (Senger et al. (1989) *Anticancer Res.* 48:1291).

The marked induction of osteopontin during arterial wound healing, immune response, and bone development and remodeling, suggests a role for this protein in these processes. Osteopontin expression by smooth muscle cells is induced upon arterial injury were it is chemotactic to smooth muscle cells and supports the adhesion of endothelial cells. Osteopontin is also abundant in athrosclerotic plaques. Secretion of osteopontin in the early response after T-cell activation is associated with enhanced secretion of IgM and IgG by B-cells (Lampe et al. (1991) *J. Immunol.* 147:2902) and is chemotactic to macrophages (Singh et al. (1989) *Anticancer Res.* 48:1291). It is constitutively expressed in $CD^{4-}CD^{8-}$ T lymphocytes from the spontaneously autoimmune MRL/1pr mouse strain (Patarca et al. (1990) *J. Exp. Med.* 172:1177–1183). Its circulating levels are elevated in individuals with autoimmune diseases. Osteopontin is also involved in bone development and remodeling. Osteopontin supports the migration and adhesion of osteoclasts and osteoblasts and appears to be chemotactic to osteoprogenitor cells.

Osteopontin is also elevated in sera from patients with advanced metastatic cancer and cellular transformation may lead to enhanced osteopontin expression and increased metastatic activity. Expression of antisense RNA in metastatic Ras transformed fibroblasts resulted in the reduction of the metastatic potential of these cells. The presence of a Gly-Arg-Gly-Asp-Ser (GRGDS, SEQ ID NO:8) cell-surface receptor binding motif within the sequence of osteopontin suggested that osteopontin may be involved in cell attachment and spreading (Oldberg et al. (1986) *Proc. Natl. Acad. Sci. USA* 83:88 19; Oldberg et al. (1986) *J. Biol. Chem.* 263:19433–19436). Osteopontin binds to cells via integrin and non-integrin receptors, and is a ligand for $\alpha_v\beta_3$, $\alpha_v\beta_1$, and $\alpha_v\beta_5$ integrins. Multiple phosphorylated and nonphosphorylated forms of osteopontin are secreted by cells and are differentially stimulated by tumor promoters (Kubota et al. (1989) Biochem. Biophys. Res. Commun. 162: 1453–1459). In addition, differential attachment of osteoclasts to surfaces coated with osteopontin isolated from various tissues and to phosphorylated and nonphosphorylated osteopontin has been demonstrated. Furthermore, cleavage of osteopontin with thrombin enhances its cell attachment properties. These results suggest that depending on the cell surface receptor repertoire, cells may recognize distinct forms of osteopontin and may respond differently to the form of osteopontin they encounter.

SUMMARY OF THE INVENTION

The present invention is based, at least in part, on the discovery of or identification of the chemotactic regions of the osteopontin polypeptide. This discovery led to the development of chemotactic peptides derived from osteopontin. The peptides (or antagonists of the same) can be used to treat conditions or diseases associated with chemotaxis. These peptides can further be used to treat conditions or diseases which can be treated using osteopontin, e.g., based upon osteopontin's chemotactic properties. For example, the peptides of the present invention can be used to treat or inhibit tumor metastasis, inflammation, osteoporosis and autoimmune disease.

The present invention pertains to osteopontin derived peptides. The peptides are capable of inducing the chemotaxis of several cell types. Examples of cell types include, but are not limited to, endothelial cells, periosteal cells, tumor cells, macrophages and osteoprogenitor cells. The osteopontin derived chemotactic peptides do not appear to mediate cell attachment but rather alter the cytoskeletal organization of the cell and induce migration.

The invention also pertains to an isolated nucleic acid encoding an osteopontin derived peptide(s) of the present invention. The nucleic acid can be used to produce the peptide and also as a therapeutic agent.

Other aspects of the invention include antibodies, e.g., monoclonal antibodies, which are specifically reactive with the above-described peptides. These antibodies can be administered to a subject in the form of a therapeutic composition to modulate the chemotactic effect of the peptides of the invention. The preferred antibody of the invention has the amino acid sequence KFHSHKDKLVLDPKSK (SEQ ID NO:2). The antibodies neutralize the migration of various cell types in response to osteopontin both in vitro and in vivo.

In another aspect, the invention features a therapeutic composition which includes an osteopontin derived chemotactic peptide and a pharmaceutically-acceptable carrier or diluent. The therapeutic composition can be used in the methods described herein.

In another aspect, the invention features a method for modulating tumor invasion in a subject. The method includes administering to a subject a therapeutically effective amount of an antagonist of an osteopontin derived chemotactic peptide such that tumor invasion is modulated.

In another aspect, the invention features a method for promoting wound healing in a subject. The method includes administering to a subject a therapeutically effective amount of a composition comprising an osteopontin derived chemotactic peptide and a pharmaceutically-acceptable carrier or diluent such that wound healing is promoted.

In another aspect, the invention features a method for modulating tumor metastasis formation. The method includes administering to a subject a therapeutically effective amount of an antibody specifically reactive with an osteopontin derived chemotactic peptide such that tumor metastasis formation is modulated.

In another aspect, the invention features a method for promoting cell migration to a target site. The method includes administering to a cell a therapeutically effective amount of an osteopontin derived chemotactic peptide such that migration of the cell to the target site is promoted.

In another aspect, the invention features a method for modulating cellular chemotaxis. The method includes administering to a cell a therapeutically effective amount of an osteopontin derived chemotactic peptide such that modulation of cellular chemotaxis occurs.

The invention also features a prosthetic device. The prosthetic device contains a therapeutically effective amount of an osteopontin derived chemotactic peptide in the prosthetic device.

In another aspect, the invention features a method for treating the formation of atherosclerotic plaques. The method includes administering to a subject a therapeutically effective amount of an osteopontin derived chemotactic peptide such that formation of artherosclerotic plaques is prevented.

In another aspect, the invention also features a method for treating an angiogenic-associated disease. The method includes administering to a subject a therapeutically effective amount of an antibody specifically reactive with an osteopontin derived chemotactic peptide such that treatment of angiogenic-associated disease occurs.

In yet another aspect, the invention features a method of inducing either in vitro or in vivo chemotaxis of a cell. The method includes administering to a cell an osteopontin derived chemotactic peptide in an amount effective to induce chemotaxis.

Other aspects of the invention include methods for inducing cell migration. The method generally includes contacting the cell, e.g., a cell involved in wound healing or a cell, e.g., a neoplastic cell, the movement of which it is desirable to control, with the osteopontin derived chemotactic peptide of the invention. The antibodies specifically reactive with the osteopontin derived peptides of the invention or antagonists thereof can also be administered to a subject having a metastatic disease, e.g., cancer, to modulate tumor invasion, e.g., to prevent or inhibit metastasis of the disease by inhibiting the chemotactic activity of osteopontin. The peptides and antibodies can be administered to the subject in the form of a therapeutic composition which includes the peptide or antibody and a pharmaceutically acceptable carrier or diluent.

The osteopontin derived chemotactic peptides and methods of the present invention are useful for modulating chemotactic activity of osteopontin. For example, osteopontin derived chemotactic peptide are useful for stimulating chemotactic activity of osteopontin. Antagonists and antibodies raised against the peptides of the invention are useful for decreasing and/or inhibiting chemotactic activity of osteopontin.

Other features and advantages of the invention will be apparent from the following detailed description, and from the claims.

DETAILED DESCRIPTION OF THE INVENTION

The present invention pertains to novel osteopontin derived peptides that induce the chemotaxis of several cell types including endothelial cells, tumor cells, macrophages and osteoprogenitor cells. Antibodies against these peptides neutralizes the migration of various cell types in response to osteopontin both in vitro and in vivo.

In accordance with this invention, an "osteopontin derived chemotactic peptide" is a peptide derived from osteopontin having chemotactic activity. Peptides of this invention include peptides comprising no more than about 60 amino acid residues and comprising at least approximately five amino acid residues in length, and preferably at least about 6–45 amino acid residues in length, and more preferably at least about 10–35 amino acid residues in length, from the C-terminal region of the osteopontin polypeptide. The term "peptides of this invention" as used herein is intended to include both peptides and analogs, e.g., agonists or antagonists, thereof. Furthermore, the peptides of the invention are not intended to include the full length osteopontin polypeptide. The peptides of the invention have chemotactic activity. Examples of the peptides of the invention include: a purified osteopontin derived chemotactic peptide comprising a sequence of the formula n-$R^1$-$R^2$-$R^3$-$R^4$-$R^5$-$R^6$-$R^7$-$R^{8}$-c, wherein $R^1$ is 0, 1, 3, 5, 10, 15, 20, 25, or 27 amino acids long; $R^2$ is Leu, Val, Met or absent; $R^3$ is Val, Leu, Ile or Met; $R^4$ is Leu, Val, Pro or Ile; $R^5$ is aspartic acid or any acidic amino acid; $R^6$ is Pro or Ser; $R^7$ is Lys, Arg, Met or Ile; $R^8$ is 0, 1, 3, 5, 10, 15, 20, 25 or 27 amino acids long, and wherein c indicates the carboxy terminal direction of the peptide and n indicates the amino terminal direction of the peptide; LVLDPK (SEQ ID NO:1); KFHSHKDKLVLDPKSK (SEQ ID NO:2); LVVDPK (SEQ ID NO:3); LVPDPK (SEQ ID NO:4); LVPDSK (SEQ ID NO:5); LVIDPK (SEQ ID NO:6); and VLDPK (SEQ ID NO:7).

The term "isolated" as used herein refers to nucleic acids of the invention which are in a non-naturally occurring form. For example, isolated DNA is a nucleic acid which is one or both of: not immediately contiguous with both of the coding sequences with which it is immediately contiguous (i.e., one at the 5' end and one at the 3' end) in the naturally-occurring genome of the organism from which the nucleic acid is derived; or which is substantially free or free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences.

The term "purified" as used herein refer to a peptide of the invention which has been treated such that the peptide is in a non-naturally occurring form. For example, the purified peptide is a peptide substantially free or free of cellular material or culture medium when produced by recombinant DNA techniques, or substantially free or free of chemical precursors or other chemicals when synthesized chemically. The language "substantially free" is defined as including preparations of the peptide of interest which preferably contain less than about 50%, more preferably less than about 40%, still more preferably less than about 30%, yet more preferably less than about 20%, and most preferably less than about 10–5% of contaminating substances. Contaminating substances are substances other than the peptide of interest.

The peptide of the invention has "chemotactic activity" if it has one or more of the following properties: (1) it has the ability to promote chemotaxis of several mammalian, e.g., human, bovine or rodent, e.g., mouse or rat, cell types responsive to osteopontin, e.g., smooth muscle cells, endothelial cells, periosteal cells, macrophages, vascular cells, cancerous cells, e.g., osteosarcoma cells, breast carcinoma cells, colon carcinoma cells, adenocarcinoma cells, and osteoprogenitor cells; (2) it has the ability to promote wound healing; (3) it has the ability to induce cell migration; (4) it has the ability to modulate, e.g., prevent or inhibit, tumor invasion or metastasis; (5) it has the ability to induce the migration of approximately about 10%, more preferably of approximately about 15% or 25%, most preferably of approximately about 50%, 75% or 85% of the cells in a given sample when assayed in a Boyden chamber assay as outlined in Example 4 below.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes therapeutic treatments, e.g., the administration of a therapeutic agent or substance, e.g., a drug. The term "treatment" as used herein is intended to include both treatment or prevention of the particular condition or disease of interest.

Isolated osteopontin derived chemotactic peptides of the invention can be produced by recombinant DNA techniques in a host cell transformed with a nucleic acid having a sequence encoding such peptide. The isolated peptides of the invention can also be produced by chemical synthesis. When a peptide is produced by recombinant techniques, host cells transformed with a nucleic acid having a sequence encoding a peptide of the invention the functional equivalent of the nucleic acid sequence are cultured in a medium suitable for the cells and peptides can be purified from cell culture medium, host cells, or both using techniques known in the art for purifying peptides and proteins including ion-exchange chromatography, gel filtration chromatography, ultrafiltration, electrophoresis or immunopurification with antibodies specific for the peptide, the protein allergen from which the peptide is derived, or a portion thereof.

The present invention provides expression vectors and host cells transformed to express the nucleic acid sequences of the invention. Nucleic acid coding for an osteopontin derived chemotactic peptide of the invention or at least one fragment thereof may be expressed in bacterial cells such as E. coli, insect cells, yeast, or mammalian cells such as Chinese hamster ovary cells (CHO). Suitable expression vectors, promoters, enhancers, and other expression control elements may be found in Sambrook et al. *Molecular Cloning: A Laboratory Manual,* second edition, Cold Spring Harbor Laboratory Press, Cold Spring Harbor, N.Y., 1989. Other suitable expression vectors, promoters, enhancers, and other expression elements are known to those skilled in the art. Expression in mammalian, yeast or insect cells leads to partial or complete glycosylation of the recombinant material and formation of any inter- or intra-chain disulfide bonds. Suitable vectors for expression in yeast include YepSec1 (Baldari et al. (1987) *Embo J.* 6: 229–234); pMFa (Kurjan and Herskowitz (1982) *Cell* 30: 933–943); JRY88 (Schultz et al. (1987) *Gene* 54: 113–123) and pYES2 (Invitrogen Corporation, San Diego, Calif.). These vectors are freely available. Baculovirus and mammalian expression systems are also available. For example, a baculovirus system is commercially available (PharMingen, San Diego, Calif.) for expression in insect cells while the pMSG vector is commercially available (Pharmacia, Piscataway, N.J.) for expression in mammalian cells.

For expression in *E. coli,* suitable expression vectors include, among others, pTRC (Amann et al. (1988) *Gene* 69: 301–315); pGEX (Amrad Corp., Melbourne, Australia); pMAL (N.E. Biolabs, Beverly, Mass.); pRIT5 (Pharmacia, Piscataway, N.J.); pET-11d (Novagen, Madison, Wis.) Jameel et al., (1990) *J. Virol.* 64:3963–3966; and pSEM (Knapp et al. (1990) *BioTechniques* 8: 280–281). The use of pTRC, and pET-11d, for example, will lead to the expression of unfused protein. The use of pMAL, pRIT5 pSEM and pGEX will lead to the expression of peptide fused to maltose E binding protein (pMAL), protein A (pRIT5), truncated β-galactosidase (PSEM), or glutathione S-transferase (pGEX). When an osteopontin derived chemotactic peptide of the invention is expressed as a fusion protein, it is particularly advantageous to introduce an enzymatic cleavage site at the fusion junction between the carrier protein and osteopontin derived chemotactic peptide. The osteopontin derived chemotactic peptide may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from, for example, Sigma Chemical Company, St. Louis, Mo. and N.E. Biolabs, Beverly, Mass. The different vectors also have different promoter regions allowing constitutive or inducible expression with, for example, IPTG induction (PRTC, Amann et al., (1988) supra; pET-11d, Novagen, Madison, Wis.) or temperature induction (pRIT5, Pharmacia, Piscataway, N.J.). It may also be appropriate to express recombinant osteopontin derived chemotactic peptides in different *E. coli* hosts that have an altered capacity to degrade recombinantly expressed proteins (e.g. U.S. Pat. No. 4,758,512). Alternatively, it may be advantageous to alter the nucleic acid sequence to use codons preferentially utilized by *E. coli,* where such nucleic acid alteration would not affect the amino acid sequence of the expressed peptide.

Host cells can be transformed to express the nucleic acid sequences of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks. The nucleic acid sequences of the invention may also be chemically synthesized using standard techniques (i.e. solid phase synthesis).

The present invention also provides nucleic acid sequences encoding peptides of the invention. Nucleic acid sequences used in any embodiment of this invention can be cDNA obtained from cDNAs encoding the corresponding peptide sequences, or alternatively, can be any oligodeoxynucleotide sequence having all or a portion of a sequence represented herein, or their functional equivalents. Such oligodeoxynucleotide sequences can be produced chemically or mechanically, using known techniques. A functional equivalent of an oligonucleotide sequence is one which is 1) a sequence capable of hybridizing to a complementary oligonucleotide to which the sequence (or corresponding sequence portions) of osteopontin derived chemotactic peptide, or fragments thereof, hybridizes, or 2) the sequence (or corresponding sequence portion) complementary to the nucleic acid sequences encoding the peptide sequence of osteopontin derived chemotactic peptide, a sequence which encodes a product (e.g., a peptide) having the same functional characteristics of the product encoded by the sequence (or corresponding sequence portion) of osteopontin derived chemotactic peptide. Whether a functional equivalent must meet one or both criteria will depend on its use (e.g., if it is to be used only as an oligoprobe, it need meet only the first or second criteria and if it is to be used to produce an osteopontin derived chemotactic peptide of the invention, it need only meet the third criterion).

The present invention also provides a method of producing isolated osteopontin derived chemotactic peptides of the invention or portions thereof comprising the steps of culturing a host cell transformed with a nucleic acid sequence encoding an osteopontin derived chemotactic peptide of the invention in an appropriate medium to produce a mixture of cells and medium containing said osteopontin derived chemotactic peptide; and purifying the mixture to produce substantially pure osteopontin derived chemotactic peptide. Host cells transformed with an expression vector containing DNA coding for an osteopontin derived chemotactic peptide of the invention or a portion thereof are cultured in a suitable medium for the host cell. Osteopontin derived chemotactic peptides of the invention can be purified from cell culture medium, host cells, or both using techniques known in the art for purifying peptides and proteins including ion-exchange chromatography, gel filtration chromatography, ultrafiltration, electrophoresis and immunopurification with antibodies specific for the osteopontin derived chemotactic peptides or portions thereof of the invention.

Methods for introducing nucleic acid (e.g., DNA) into cells have been described extensively in the art. Many of these methods can be applied to cells either in vitro or in vivo. Non-limiting examples of techniques which can be used to introduce an expression vector encoding a peptide or antibody of the invention into a host cell include:

Naked DNA can be introduced into cells by complexing the DNA to a cation, such as polylysine, which is then coupled to the exterior of an adenovirus virion (e.g., through an antibody bridge, wherein the antibody is specific for the adenovirus molecule and the polylysine is covalently coupled to the antibody) (see Curiel, D. T., et al. (1992) *Human Gene Therapy* 3:147–154). Entry of the DNA into cells exploits the viral entry function, including natural disruption of endosomes to allow release of the DNA intracellularly. A particularly advantageous feature of this approach is the flexibility in the size and design of heterologous DNA that can be transferred to cells.

Naked DNA can also be introduced into cells by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. Receptors to which a DNA-ligand complex can be targeted include the asialoglycoprotein receptor for hepatocytes, mannose for macrophages (lymphoma), mannose 6-phosphate glycoproteins for fibroblasts (fibrosarcoma), intrinsic factor-vitamin B12 and bile acids (See Kramer et al. (1992) *J. Biol. Chem.* 267:18598–18604) for enterocytes, insulin for fat cells, and transferrin for smooth muscle cells or other cells bearing transferrin receptors. Additionally, a DNA-ligand complex can be linked to adenovirus capsids which naturally disrupt endosomes, thereby promoting release of the DNA material into the cytoplasm and avoiding degradation of the complex by intracellular lysosomes (see for example Curiel et al. (1991) *Proc. Natl. Acad. Sci. USA* 88:8850; and Cotten, M. et al. (1992) *Proc. Natl. Acad. Sci. USA* 89:6094–6098; et al. (1992) *Proc. Natl. Acad. Sci. USA* 89:6099–6103). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Naked DNA can be introduced into cells by mixing the DNA with a liposome suspension containing cationic lipids. The DNA/liposome complex is then incubated with cells. Liposome mediated transfection can be used to stably (or transiently) transfect cells in culture in vitro. Protocols can be found in *Current Protocols in Molecular Biology*, Ausubel, F. M. et al. (eds.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157–176; Wang and Huang (1987) *Proc. Natl. Acad. Sci. USA* 84:7851–7855; Brigham et al. (1989) *Am. J. Med. Sci.* 298:278; and Gould-Fogerite et al. (1989) *Gene* 84:429–438.

Naked DNA can be introduced into cells by directly injecting the DNA into the cells. For an in vitro culture of cells, DNA can be introduced by microinjection, although this not practical for large numbers of cells. Direct injection has also been used to introduce naked DNA into cells in vivo (see e.g., Acsadi et al. (1991) *Nature* 332: 815–818; Wolff et al. (1990) *Science* 247:1465–1468). A delivery apparatus (e.g., a "gene gun") for injecting DNA into cells in vivo can be used. Such an apparatus is commercially available (e.g., from BioRad).

Defective retroviruses are well characterized for use in gene transfer for gene therapy purposes (for a review see Miller, A. D. (1990) *Blood* 76:271). A recombinant retrovirus can be constructed having a nucleic acid encoding a gene of interest (e.g., a gene encoding a peptide or antibody of interest) inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al.

(1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

The genome of an adenovirus can be manipulated such that it encodes and expresses a gene product of interest (e.g., peptides of SEQ ID NOs:1–7 or other peptides of the requisite homology thereto or an antibody which recognizes such peptides) but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to many other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that can integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of the introduced DNA can be detected, for example, by Northern blotting, RNase protection or reverse transcriptase-polymerase chain reaction (RT-PCR). Expression of the introduced gene product (e.g., the peptide of interest) in the cell can be detected by an appropriate assay for detecting proteins, for example by immunohistochemistry.

As will be appreciated by those skilled in the art, the choice of expression vector system will depend, at least in part, on the host cell targeted for introduction of the nucleic acid. For example, nucleic acids encoding peptides or antibodies of the invention can preferably be administered such that they are expressed in neoplastic cells, e.g., carcinoma cells derived from tissues or organs including breast, testis, ovary, lung, gastrointestinal tract, which spread from one location to another. Alternatively, nucleic acids encoding peptides or antibodies of the invention can be targeted for introduction into cells, such as extracellular matrix cells (connective tissue cells) involved in wound healing, to thereby promote recovery from wounds.

The invention also includes antibodies specifically reactive with osteopontin derived chemotactic peptides of the invention. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject osteopontin derived chemotactic peptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the osteopontin derived chemotactic peptide of the invention, e.g. antigenic determinants of a peptide of SEQ ID NOs:1–7.

The term "antibody", as used herein, is intended to include fragments thereof which are also specifically reactive with an osteopontin derived chemotactic peptide. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Both monoclonal and polyclonal antibodies (Ab) directed against the osteopontin derived chemotactic peptides, or fragments or analogs thereof, and antibody fragments such as Fab' and F(ab')$_2$, can be used to block the action of osteopontin and allow the study of the role of the ospteopontin derived chemotactic peptides of the present invention.

Antibodies which specifically bind osteopontin epitopes can also be used in immunohistochemical staining of tissue samples in order to evaluate the abundance and pattern of expression of osteopontin. Anti-osteopontin derived chemotactic peptide antibodies can be used diagnostically in immuno-precipitation and immuno-blotting to detect and evaluate wild type or mutant osteopontin polypeptide levels in tissue or bodily fluid as part of a clinical testing procedure. Likewise, the ability to monitor osteopontin levels in an individual can allow determination of the efficacy of a given treatment regimen for an individual afflicted with disorders associated with tumor metastases. The level of osteopontin can be measured in tissue, such as produced by biopsy.

Another application of anti-osteopontin derived chemotactic peptide antibodies of the present invention is in the immunological screening of cDNA libraries constructed in expression vectors such as lgt11, lgt18–23, 1ZAP, and 1ORF8. Messenger libraries of this type, having coding sequences inserted in the correct reading frame and orientation, can produce fusion proteins. For instance, lgt11 will produce fusion proteins whose amino termini consist of β-galactosidase amino acid sequences and whose carboxy termini consist of a foreign polypeptide. Antigenic epitopes of a subject osteopontin derived chemotactic peptide can then be detected with antibodies, as, for example, reacting nitrocellulose filters lifted from infected plates with anti-osteopontin derived chemotactic peptide antibodies. Phage, scored by this assay, can then be isolated from the infected plate. Thus, the presence of osteopontin homologs can be detected and cloned from other animals, and alternate isoforms (including splicing variants) can be detected and cloned from human sources.

The invention also includes analogs, preferably biologically active analogs of the osteopontin derived chemotactic peptides of the invention. A biologically active analog is one having any in vivo or in vitro activity which is characteristic of the osteopontin derived chemotactic peptide of the invention, e.g., one or more of the biological activities described above. Most preferably the analog possesses about 10%, preferably about 40%, or at least about 90% of the activity of the osteopontin derived chemotactic peptide of the invention in any in vivo or in vitro chemotactic activity assay.

Analogs can differ from an osteopontin derived chemotactic peptide of the invention in amino acid sequence or in ways that do not involve sequence, or both. Non-sequence modifications include in vivo or in vitro chemical derivatization of an osteopontin derived chemotactic peptide of the invention. Non-sequence modifications include changes in acetylation, methylation, phosphorylation, carboxylation, or glycosylation.

It is also possible to modify the structure of a peptide of the invention for such purposes as increasing solubility, enhancing therapeutic or preventive efficacy, or stability (e.g., shelf life ex vivo and resistance to proteolytic degradation in vivo ). A modified peptide can be produced in which the amino acid sequence has been altered, such as by amino acid substitution, deletion, or addition, to modify immunogenicity, or to which a component has been added for the same purpose.

Additionally, peptides of the invention can be modified by replacing an amino acid shown to be essential for chemotactic activity with another, preferably similar amino acid residue (conservative substitution) whose presence is shown to enhance, diminish but not eliminate or not affect chemotactic activity.

In order to enhance stability and/or reactivity, peptides of the invention can also be modified to incorporate one or more polymorphisms in the amino acid sequence of the peptide resulting from natural allelic variation. Additionally, D-amino acids, non-natural amino acids or non-amino acid analogues can be substituted or added to produce a modified peptide within the scope of this invention. Furthermore, peptides of the present invention can be modified using the polyethylene glycol (PEG) method of A. Sehon and co-workers (Wie et al. supra) to produce a protein or peptide conjugated with PEG. In addition, PEG can be added during chemical synthesis of a protein or peptide of the invention. Modifications of peptides or portions thereof can also include reduction/alyklation (Tarr in: *Methods of Protein Microcharacterization*, J. E. Silver ed. Humana Press, Clifton, N.J., pp 155–194 (1986)); acylation (Tarr, supra); chemical coupling to an appropriate carrier (Mishell and Shiigi, eds, *Selected Methods in Cellular Immunology*, WH Freeman, San Francisco, Calif. (1980); U.S. Pat. No. 4,939, 239; or mild formalin treatment (*Marsh International Archives of Allergy and Applied Immunology*, 41:199–215 (1971)).

To facilitate purification and potentially increase solubility of peptides of the invention, it is possible to add reporter group(s) to the peptide backbone. For example, polyhistidine can be added to a peptide to purify the peptide on immobilized metal ion affinity chromatography (Hochuli, E. et al., *Bio/Technology*, 6:1321–1325 (1988)). In addition, specific endoprotease cleavage sites can be introduced, if desired, between a reporter group and amino acid sequences of a peptide to facilitate isolation of peptides free of irrelevant sequences.

Site-directed mutagenesis of DNA encoding a peptide of the invention can be used to modify the structure of the peptide by methods known in the art. Such methods may, among others, include PCR with degenerate oligonucleotides (Ho et al., *Gene*, 77:51–59 (1989)) or total synthesis of mutated genes (Hostomsky, Z. et al., *Biochem. Biophys, Res. Comm.*, 161:1056–1063 (1989)). To enhance bacterial expression, the aforementioned methods can be used in conjunction with other procedures to change the eucaryotic codons in DNA constructs encoding protein or peptides of the invention to ones preferentially used in *E. coli*, yeast, mammalian cells, or other eukaryotic cells.

Peptides or antibodies of the present invention can also be used for detecting inflammation. For example, this could be done by combining blood or blood products obtained from an individual with an isolated osteopontin derived chemotactic peptide, under conditions appropriate for binding of components in the blood (e.g., antibodies, T-cells, B-cells) with the peptide(s) and determining the extent to which such binding occurs.

The osteopontin derived chemotactic peptides of the invention can be used in methods of diagnosing, treating and preventing tumor metastasis, inflammation, osteoporosis and immune diseases. Thus the present invention provides therapeutic compositions comprising isolated peptides or analogs thereof produced in a host cell transformed to express such osteopontin derived chemotactic peptide or analogs thereof and a pharmaceutically acceptable carrier, or diluent. The therapeutic compositions of the invention may also comprise synthetically prepared osteopontin derived chemotactic peptides or analogs thereof and a pharmaceutically acceptable carrier or diluent. Administration of the therapeutic compositions of the present invention to an individual can be carried out using known techniques. Osteopontin derived chemotactic peptides or analogs thereof may be administered to an individual in combination with, for example, an appropriate diluent, adjuvant and/or a carrier. Pharmaceutically acceptable diluents include saline and aqueous buffer solutions. Pharmaceutically acceptable carriers include polyethylene glycol (Wie et al. (1981) *Int. Arch. Allergy Appl. Immunol.* 64:84–99) and liposomes (Strejan et al. (1984) *J. Neuroimmunol* 7: 27). The carrier can also include a matrix, e.g., fibrin, collagen, gelatin, agarose, calcium phosphate containing compounds and combinations thereof. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether.

Administration of the therapeutic compositions of the present invention to an individual can be carried out using known procedures at dosages and for periods of time effective to significantly reduce or eliminate symptoms associated with the condition or disease being treated. Effective amounts of the therapeutic compositions will vary according to the age, sex, and weight of the "subject", and the ability of the osteopontin derived chemotactic peptide to perform its intended function.

The term "subject" is intended to include subjects susceptible to the particular condition or disease being treated. The term "subject" is intended to include mammals, particularly humans. An examples of a subject includes a mammal susceptible to metastatic disease, e.g, cancer. Another example of a subject includes a mammal capable of being wounded or a mammal with persistent, slow-healing wounds. For example, the therapeutic compositions can be administered to promote wound healing or prevent or inhibit metastasis of neoplastic cells.

In addition to compositions containing a single peptide, mixtures of at least two peptides (i.e., a physical mixture of at least two peptides) can also be provided. Such compositions can be administered in the form of a therapeutic composition with a pharmaceutically acceptable carrier or diluent. A therapeutically effective amount of one or more of such compositions can be administered simultaneously or sequentially. Preferred therapeutic compositions comprise peptides which include the peptides having the amino acid sequences shown in SEQ ID NOs:1–7. Dosage regima may be adjusted to provide the optimum therapeutic response. For example, several divided doses may be administered daily or the dose may be proportionally reduced as indicated by the exigencies of the therapeutic situation. A therapeutically effective amount is that amount sufficient to significantly reduce or alleviate symptoms associated with the particular condition or disease being treated. A preferred composition of the present invention is a wound healing composition. The wound healing composition contains a wound healing effective amount of osteopontin derived chemotactic peptide of the invention.

The active compound (i.e., peptide or fragment thereof) may be administered in a convenient manner such as by injection (subcutaneous, intravenous, etc.), oral administration, inhalation, transdermal application, or rectal administration. Depending on the route of administration, the active compound may be coated within a material to protect the compound from the action of enzymes, acids and other natural conditions which may inactivate the compound.

To administer a peptide by other than parenteral administration, it may be necessary to coat the protein with, or co-administer the protein with, a material to prevent its inactivation. For example, peptide or portion thereof may be co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.* 7:27).

The active compound may also be administered parenterally or intraperitoneally. Dispersions can also be prepared in glycerol, liquid polyethyline glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions of dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glyceral, propylene glycol, and liquid polyetheylene glycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thirmerosal, and the like. In many cases, it will be preferable to include isotonic agents, for example, sugars, polyalcohols such as manitol and sorbitol or sodium chloride in the composition. Prolonged absorption of the injectable compositions can be brought about, including in the composition, an agent which delays absorption, for example, aluminum monostearate and gelatin.

Sterile injectable solutions can be prepared by incorporating active compound (i.e., peptide or fragment thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., peptide or fragment thereof) plus any additional desired ingredient from a previously sterile-filtered solution thereof.

When a peptide of the invention is suitably protected, as described above, the peptide may be orally administered, for example, with an inert diluent or an assimilable edible carrier. The peptide and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the composition and preparations may, of course, be varied and may conveniently be between about 5 to 80% of the weight of the unit. The amount of active compound in such therapeutically useful compositions is such that a suitable dosage will be obtained.

The tablets, troches, pills, capsules and the like may also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservative, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered topically. The use of a non-ageous lipid miscible carrier, for example, such as prepared with liposomes are particularly advantageous since they provide improved activity at the treatment site (e.g., the wound site).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit from as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the novel dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The osteopontin derived chemotactic peptides of the invention or analogs thereof can be used to coat a prosthetic device. It is not necessary for the osteopontin derived chemotactic peptide of the invention to be covalently attached to the surface toward which chemotaxis is being stimulated. It is sufficient that the peptide be present at the surface. Therefore, the phrase "the incorporation of an osteopontin derived chemotactic peptide in the prosthetic device" as used herein encompasses all methods of applying an osteopontin derived chemotactic peptide of this invention to a surface, whether that application results in chemical bonding or not. For example, solutions or suspensions containing the peptide can be painted on the surface of a prosthetic device or a device can be submerged in a solution of the chemotactic peptide.

It is also possible to form covalent bonds between the osteopontin derived chemotactic peptide and the prosthetic device. For example, during the synthesis of an osteopontin derived chemotactic peptide as described above, various intermediates are produced which have reactive carboxy or amino terminals. Many of the prosthetic devices which are intended for incorporation into regenerating tissue are prepared from collagen or related materials and therefore contain free amino acid functional groups, such as amino or carboxylic acid groups. Peptide bonds can easily be formed between such functional groups in the prosthetic device and reactive intermediates such as those described above.

The type of prosthetic device which can be used in conjunction with the present invention is not limited, since the chemotactic property is related to the peptide and not to the prosthetic device itself. It is preferred, however, that the prosthetic device be one which is intended for incorporation into regenerating tissue, such as an artificial vein or artery or artificial skin. Other useful prosthetic devices include artificial hips and artificial knees. The most commonly used fabric for blood vessel prosthesis is made from Dacron (Trademark, DuPont), a synthetic polyester fiber made from polyethylene terephthalate. Dacron has been used in several weaves and in combination with other materials. An example of a frequently used material is the DeBakey Elastic Dacron fabric manufactured by USCI, a division of C.R. Bard, Inc. (Cat. No. 007830). Other commonly used materials are felted polyurethane and polytetrafluorethylene (Berkowitz et al, *Surgery,* 72, 221 (1972); Wagner et al, *J.*

*Surg. Res.,* 1, 52 (1956); Goldfarb et al, *Trans Am. Soc. Art. Int. Org.,* XXIII, 268 (1977)). No chemotactic substance is normally used with these materials.

Another recent development in prosthetic devices is artificial skin of the type disclosed in Yannas and Burke, *J. Biomed. Mat. Res.,* 14, 65–81 (1980). The artificial skin is a collagen/glycosaminoglycan (GAG) composite and had been successfully tested as full-thickness skin wound replacements. Such membranes have effectively protected wounds from infection and fluid loss for long periods of time without rejection and without requiring change or other invasive manipulation. Appropriately designed artificial skin of this type has retarded the wound contraction, and the artificial skin has been replaced, at least in part, by newly synthesized connective tissue. Additional disclosure of this artificial skin is found in Yannas et al, ibid, 107–131 (1980), and Dagalakis et al, ibid, 511–528 (1980). Two particularly preferred embodiments of the present invention involve using the chemotactic polypeptide with a collagen/glycosaminoglycan composite material as an artificial skin, as described in U.S. Pat. No. 4,280,954, and with biocompatible artificial materials based on polypeptides as described in U.S. Pat No. 4,187,852, all of which are herein incorporated by reference. These are peptide-containing materials, and the chemotactic polypeptide may readily be attached by covalent bonding into such materials by the methods described above. However, as also previously indicated, covalent bonding is not necessary and indeed is not preferred since the chemotactic property is also exhibited when the chemotactic peptide is merely present on the surface or in the presence of a prosthetic material. Prosthetic devices having surfaces comprising other structural peptides are also preferred over prosthetic devices having other types of surfaces, although other types of surfaces, such as Dacron, and other synthetic fibers, are specifically included. Examples include natural materials such tendons or ligaments (for example, those transferred from one location to another within the same body) and synthetic or semi-synthetic materials. Semi-synthetic materials are those derived, by manipulation of natural materials, such as collagen.

The amount of osteopontin derived chemotactic peptide which is required for a particular prosthetic device can be determined using art-recognized techniques. Generally, quite low concentrations of the chemotactic peptide are required. For example, doping of a non-chemotactic surface to produce low concentrations of 0.1 nM to 100 nM of an osteopontin derived chemotactic peptide of the invention at the surface will be sufficient.

Synthetically produced peptides of the invention comprising up to approximately forty-five amino acid residues in length, and most preferably up to approximately thirty amino acid residues in length are particularly desirable as increases in length may result in difficulty in peptide synthesis. Peptides of the invention may also be produced recombinantly as described above, and it is preferable that peptides of 45 amino acids or longer be produced recombinantly.

Peptides of the invention can also be used in methods for promoting cell migration. A preferred application of this method is promotion of wound healing in a subject capable of being wounded or a subject with persistent, slow-healing wounds. Subjects with persistent, slow healing wounds include mammals, e.g., humans in advanced stages of diabetes who have circulatory problems which prevent proper wound healing of persistent wounds on the extremities, e.g., humans with severe wounds resulting from burns, e.g., humans with severely infected wounds.

Additional uses of the antibodies specifically reactive with the osteopontin derived peptides of the invention or antagonists thereof in the form of a therapeutic composition as described above, are in methods for modulating, e.g., preventing or inhibiting tumor invasion, e.g., tumor metastasis. It is the ability to metastasize that makes cancers hard to eradicate surgically or by localized irradiation. To disseminate widely in the body, the cells of a typical solid tumor must be able to loosen their adhesion to their original neighbors, escape from the tissue of origin, burrow through other tissues until they reach a blood vessel or a lymphatic vessel, cross the basal lamina and endothelial lining of the vessel so as to enter the circulation, make an exit from the circulation elsewhere in the body, and survive and proliferate in the new environment in which they find themselves. Treatments which act at different stages of the metastasis process to prevent or inhibit spread of the tumor (neoplastic) cells are being developed. For example, it has been shown that for tumor cells to cross a basal lamina they must have laminin receptors, which enable the cells to adhere to the lamina, and they must secrete type IV collagenase, which helps them digest the lamina. Antibodies or other reagents that block either laminin attachment or the activity of type IV collagenase have been found to block metastasis in experimental animals.

The osteopontin derived chemotactic peptides of the invention can also be used for treating or preventing an angiogenic-associated disease. The process of angiogenesis, the growth of blood vessels, is fundamental to reproduction, development and repair. Under these conditions, angiogeneis is highly regulated and of short duration. In many pathologic states, the regulation is deranged so that the disease itself is driven by persistent, unabated neovascularization. Thus, tumor growth and metastasis are angiogenesis-dependent and a wide-variety of non-neoplastic diseases are dominated by uncontrolled angiogenesis. As used herein, the term "angiogenic-associated disease" refers to a disease or a condition resulting from unregulated, e.g., uncontrolled, growth of blood vessels. The term is intended to include both neoplastic and non-neoplastic diseases or conditions. For example, angiogenic-associated diseases include arthritis, psoriasis, hemangioma, cancer or tumor, e.g., solid tumor, metastasis, and ocular neovascularization.

The marked induction of osteopontin during arterial wound healing and tumor invasion and metastasis, suggests a role for this protein in these processes. Thus, the osteopontin derived chemotactic peptides of the invention can be used for stimulation or inhibition of angiogenesis. For example, antagonists of an osteopontin derived chemotactic peptide of the invention or antibodies raised against the osteopontin derived chemotactic peptides of the invention can be used as angiogenesis inhibitors in treatment of cancer, e.g., as: (1) adjuvant therapy; (2) prophylactic therapy to prevent tumor recurrence; or (3) anti-metastatic therapy.

Drug Screening Assays

By making available purified and recombinant-osteopontin derived chemotactic peptides, the present invention provides assays which can be used to screen for drugs which are either agonists or antagonists of the normal cellular function, in this case, of osteopontin. In one embodiment, the assay evaluates the ability of a compound to modulate binding between osteopontin and a naturally occurring ligand, e.g., CD44 or an integrin. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

The present invention is further illustrated by the following Examples which in no way should be construed as further limiting. The entire contents of all of the references (including literature references, issued patents, and published patent applications) cited throughout this application are hereby expressly incorporated by reference.

EXEMPLIFICATION

The sequence LVLDPK (SEQ ID NO:1) has been implicated as a chemotactic peptide in osteopontin (OPN). Antibodies against this peptide neutralize the migration of cells to OPN. This peptide also competes with OPN for the migration of cells, indicating that both molecules share a similar receptor. Replacing the ASP (D) in the sequence eliminates the chemotactic properties of the peptide. The shortest chemotactic peptide tested thus far which retains some chemotactic properties is VLDPK (SEQ ID NO:7).

Example 1

Peptide Mapping of Chemotactic Domain on Osteopontin by Tryptic Digest

Purified OPN (~0.5 mg) was digested with trypsin (2% w/w) in 0.2 ml of 50 mM $NH_4HCO_3$, pH 8.0, for 20 hours at 37° C. before treatment of the reaction products with 50 μl of 100% $H_2O$+0.1% trifluoroacidic acid (TFA) and resolution of the peptides by HPLC chromatography on C-18 column (25×0.46 cm). After injection the column was washed for 10 min, followed by linear gradient elution from 100% $H_2O$+0.1% TFA to 60% $CH_3CN$+0.55% TFA over 120 min, with a second gradient from 60% $CH_3CN$ to 80% $CN_3CN$ over 30 min at a flow rate of 0.5 ml/min. The absorbance at 219 nm was recorded continuously by an on-line chart recorder/integrator using Gilson HM Holochrome detector, and fractions of 0.5 ml were collected. Each peak was then tested for mediation of chemotaxis or for its ability to inhibit OPN mediated chemotaxis using the chemotactic assay described in Example 4 below. Furthermore, each peak was also tested for its ability to promote attachment of CD44+ or αvβx cells.

The procedure described above results in the generation of partial tryptic peptides. This is essential to ensure that a chemotactic peptide containing an ARG or LYS residue will be detected by the assay and eliminates the necessity to do multiple digests with various proteases to ensure that all possible peptides were tested.

Since the chemotactic domain was localized to the c-terminus half of the protein, the chemotactic domain was further localized by testing partial tryptic peptides generated from osteopontin for their chemotactic activity as outlined in Example 4 below. The results are outlined in Table 1.

TABLE 1

Localization of the Chemotactic Peptide in Tryptic Peptides of Osteopontin

|  |  | Lower Chamber | | | | | |
|---|---|---|---|---|---|---|---|
|  |  | PBS | peptide 49 | peptide 50 | peptide 51 | peptide 52 | peptide 53 |
| Upper Chamber | PBS | 9 | 15 | 23 | 68 | 48 | 18 |
|  | peptide 49 | 8 | 11 | 19 | 83 | 39 | 15 |
|  | peptide 50 | 6 | 17 | 22 | 56 | 28 | 11 |
|  | peptide 51 | 13 | 15 | 16 | 32 | 16 | 19 |
|  | peptide 52 | 5 | 19 | 31 | 78 | 22 | 9 |
|  | peptide 53 | 9 | 13 | 24 | 62 | 39 | 10 |

Peptide 51 showed chemotactic properties. The sequence of this peptide was determined to be LVLDPK (SEQ ID NO:1).

Example 2

Peptide Mapping of the Chemotactic Domain on Osteopontin by Use of Synthetic Peptides Positive peaks from tryptic digest were sequenced by gas-phase automated sequenator. Chemotactic peptides corresponding to the positive sequences were synthesized and the resulting synthetic peptides were then tested for their ability to promote either chemotaxis or to inhibit the chemotaxis to OPN as described in Example 4. Chemical synthesis of peptides provides a convenient method to test the sequence specificity and minimal length of the chemotactic peptides. The results are outlined in Table 2.

TABLE 2

Chemotactic Properties of Synthetic Peptides

|  |  | Lower Chamber | | | |
|---|---|---|---|---|---|
|  |  | PBS | peptide 51 | SP64 | OPN |
| Upper Chamber | PBS | 12 | 128 | 117 | 118 |
|  | peptide 51 | 9 | 51 | 40 | 32 |

TABLE 2-continued

Chemotactic Properties of Synthetic Peptides

|  | Lower Chamber | | | |
|---|---|---|---|---|
|  | PBS | peptide 51 | SP64 | OPN |
| SP64 | 4 | 47 | 66 | 45 |
| OPN | 21 | 88 | 74 | 43 |

OPN = osteopontin

The migration of osteosarcoma cells to the lower side of the filter in response to chemotactic agent and the inhibition of chemotaxis by addition of chemotactic agent to the upper chamber supports the conclusion that the observed phenomena is chemotaxis and not random migration. SP64 is a synthetic peptide containing the chemotactic sequence and having the sequence KFHSHKDKLVLDPKSK (SEQ ID NO:2).

Example 3

Production of Antibodies Against Specific Osteopontin Epitopes

Positive synthetic peptide SP64 from Example 2 above was conjugated to BSA and polyclonal antibodies were raised in rabbits. The resulting plasma containing antibodies against the synthetic peptide was purified by affinity chromatography on a sepharose 4B column conjugated with the relevant peptide. The resulting affinity purified antibody was then tested for its ability to inhibit the chemotaxis of to OPN.

The resulting immune sera contained antibodies against the synthetic peptide and specifically recognized OPN. Antibodies against the synthetic peptide neutralized the migration of osteosarcoma cells to OPN, synthetic peptides, and OPN(ct) when placed either in the upper or lower chambers of the Boyden chamber. It is assumed that the antibody complexes with the chemotactic domain and prevents its recognition by the chemotactic receptor. The results are outlined in Table 3.

TABLE 3

Inhibition of Osteopontin and Osteopontin Derived Chemotaxis by Ab64

|  |  | Lower Chamber | | | |
|---|---|---|---|---|---|
|  |  | PBS | OPN | peptide 51 | Ab64 |
| Upper Chamber | PBS | 21 | 217 | 243 | 15 |
|  | OPN | 14 | 94 | 187 | 26 |
|  | peptide 51 | 8 | 65 | 109 | 2 |
|  | Ab64 | 16 | 51 | 62 | 9 |

OPN = osteopontin, Ab64 = antibody raised against the SP64 synthetic peptide.

Chemotaxis was assessed as described in Example 4. Antibodies against the SP64 chemotactic peptide neutralize the chemotaxis of osteosarcoma cells to OPN, SP64, peptide 51, and OPN(ct).

Example 4

Adherence and Spreading of Cells 48 well plates were coated with either 10 ug/ml of osteopontin or 10 ug/ml fibronectin for 18 hours at 4° C. followed by blocking with 1 mg/ml BSA for two hours at room temperature. 1000 cells/well were incubated at 37° C. in calcium-free magnesium-free PBS containing 100 µg/ml BSA. After 30 min the cells were fixed in 4% paraformaldehyde in PBS containing 10% sucrose and stained with toluidine blue and hematoxilin. Attachment was assessed by counting the total number of cells per well. Spreading was assessed by the number of attached cells that spread on OPN or Fibronectin.

Chemotaxis of Osteosarcoma Cells in Response to Osteopontin

In a modified Boyden chamber, both surfaces of polycarbonate filters (pore size, 8 μm) were coated with gelatin (100 μg/ml, overnight) before 1×10³ osteosarcoma cells were added in 500 μl to the upper chamber and incubated at 37° C. in the presence or absence of chemotactic agents in the lower chamber. After two hours, the membranes were fixed in methanol and stained with hematoxilin/toluidine blue. Responding cells on the lower surface of the filter were counted microscopically and evaluated in triplicates. Random migration was assessed by counting the number of cells that migrated to the lower surface of the filter when excess chemotactic molecule was added to the upper chamber. Averages from at least three experiments were averaged and are presented in Table 4.

TABLE 4

Chemotactic properties of Osteopontin

| | | Lower Chamber | | | |
|---|---|---|---|---|---|
| | | PBS | OPN(nT) | OPN(ct) | OPN |
| Upper Chamber | PBS | 28 | 12 | 117 | 98 |
| | OPN(ct) | 156 | 128 | 31 | 58 |
| | OPN(nT) | 4 | 17 | 76 | 115 |
| | OPN | 21 | 13 | 74 | 43 |

Osteosarcoma cells chemotax toward osteopontin (OPN), and OPN(ct), the C-terminal half of OPN after thrombin cleavage, but not to OPN(nT), the N-terminal half that contains the RGD sequence.

Several additional cell types, e.g., smooth muscle cells, endothelial cells, macrophages, breast carcinoma cells, colon carcinoma cells, adenocarcinoma cells and osteoprogenitor cells, were also tested for their ability to chemotax to peptide 51.

Haptotaxis

To assess haptotaxis the lower surface of the filters were coated overnight with 10 μg/nl of the chemotactic agent. The filters were allowed to air dry for one hour before use. 1000 cells were added to the upper chamber and the Boyden chamber (reference) was incubated at 37° C. for two hours in the absence of chemotactic peptide in the lower chamber. Cells that have migrated to the bottom of the filter were then assessed as described above.

Spreading

Spreading of cells was determined one hour after attachment of cells to OPN or peptides or modified OPN by assessing the formation of focal adhesion plaques.

Example 5

Mutational Analysis

To determine the sequence specificity of the chemotactic peptide (peptide 51), several sequence specific peptides were synthesized and tested for their ability to induce chemotaxis of osteosarcoma cells. The sequence of the positive peptides is given in Table 5 below. The only peptide that failed to induce chemotaxis had the sequence LVLAPK (SEQ ID NO:9), thus the aspartic acid (D) in the sequence appears to be necessary for activity.

TABLE 5

Sequence of Chemotactic Peptides

| | Chemotactic Peptides |
|---|---|
| peptide 51 | LVLDPK (SEQ ID NO:1) |
| SP64 | KFHSHKDKLVLDPKSK (SEQ ID NO:2) |
| peptide A | LVVDPK (SEQ ID NO:3) |
| peptide B | LVPDPK (SEQ ID NO:4) |
| peptide C | LVPDSK (SEQ ID NO:5) |
| peptide D | LVIDPK (SEQ ID NO:6) |
| peptide E | VLDPK (SEQ ID NO:7) |

The shortest chemotactic peptide is VLDPK (peptide E) (SEQ ID NO:7) which retains some chemotactic activity.

Example 6

In Vivo Cellular Migration

Boyden chamber experiments have indicated that osteopontin elicits a migration of a cellular population predominantly comprised of Mac-1+CD44+ cells. Thus, it was investigated whether a similar population of cells was attracted in vivo following intraperitoneal injection with osteopontin.

Mice were injected intraperitoneally with varying dosages of K7 osteosarcoma-derived osteopontin. All injection volumes were 200 μl. Injections of vehicle alone (PBS) served as negative controls and vehicle plus 20 μg lipopolysaccharide (LPS) injections served as positive controls for elicitation of peritoneal exudates.

Mice were sacrificed by $CO_2$-asphyxiation at varying times following injection. Immediately after sacrifice, peritoneal exudate was recovered by intraperitoneal injection and recovery of 10 mL PBS. The lavage procedure was performed twice on each mouse. Following this, red blood cells were lysed by hypotonic lysis with ACK lysis buffer (0.15 M $NH_4Cl$, 1.0 mM $KHCO_3$, 0.1 mM $Na_2EDTA$, pH 7.4) for 5 minutes at room temperature, and the preparation was washed in DMEM, 5% FBS. Cells were resuspended in DMEM, 5% FBS for fluorescent antibody staining.

Each sample of cells to be analyzed for specific surface markers was suspended in DMEM, 5% FBS at a concentration of 0.2 to 1 million cells in 50 μl. Fluorescence-labeled antibodies were added at 1 μg/1×10⁶ cells, and incubated with the cells for 30 minutes at 4° C. Samples were washed twice with 200 μl of PBS following antibody staining and fixed with 500 μl of 2% paraformaldehyde in PBS. Peritoneal exudate cells were analyzed by dual-color flow cytometry for expression of CD44 (PE), CD11b (Mac-1, FITC, macrophage marker), B220 (FITC, B-cell marker), and CD3 (FITC, T-cell marker). All antibodies were purchased from PharMingen and flow cytometric analysis was done using a Coulter EPICS flow cytometer. Controls for non-specific binding and single color controls were included.

Titration of soluble osteopontin into the peritoneum resulted in a dose dependent increase in the cellular infiltrate 6 hours after injection, with a peak response occurring at a dose around 13 μg. The number of Mac-1+ cells in the infiltrate increased fivefold over basal levels during this time while the number of CD3+ and B220+ cells was only marginally elevated. A nearly sixfold reduction in number of CD44+ Mac1+ cells also occurred at a dose around 7 μg, forming a relatively sharp peak response that decreased at higher doses. Preferential attraction of Mac1+ and CD44+ cells at a relatively low dosage indicates that i.p. inoculation of osteopontin at this level is likely to elicit a lineage-specific chemotactic response as opposed to a generalized inflammatory response. These data support the observations made in the in vitro splenocyte chemotaxis assays that the predominant cell population to migrate in response to phosphorylated osteopontin is comprised of Mac-1+ CD44+ cells.

To further characterize the effects of osteopontin on in vivo cellular migration, a time course experiment was performed using an osteopontin dosage that elicited peak levels of infiltration. The total cellular response to osteopontin administration peaked sharply at 4 to 6 hours. This is likely to be due to a high rate of clearance from the peritoneal cavity. Co-injection of osteopontin with anti-osteopontin antibody described herein in Example 3 prevented the influx of cells whereas rabbit immunoglobulin had no effect (PBS 178 250 cells, OPN 1.16 million cells, OPN+anti-OPN 534 750 cells, OPN+Ig 922 250 cells, PBS+Ig 496 000 cells). The ability of the anti-osteopontin antibody to diminish the observed chemotactic response in vivo demonstrates the in vivo specificity of osteopontin.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

---

What is claimed is:

1. A purified peptide consisting of the amino acid sequence LVLDPK (SEQ ID NO:1).

2. A purified peptide consisting of the amino acid sequence VLDPK (SEQ ID NO:7).

3. A purified peptide consisting essentially of a sequence selected from the group consisting of LVLDPK (SEQ ID NO:1), LVVDPK (SEQ ID NO:3), LVPDPK (SEQ ID NO:4), LVPDSK (SEQ ID NO:5) and LVIDPK (SEQ ID NO:6, wherein the peptide consists of between 6 and 60 amino acids, wherein the peptide has chemotactic activity.

4. A purified peptide comprising 60 amino acids or less and the sequence VLDPK (SEQ ID NO:7), said peptide having chemotactic activity.

5. A composition comprising an amount of the peptide of claim 3 or 4 suitable to effect chemotaxis of cells bearing receptors that recognize the peptide and pharmaceutically-acceptable carrier or diluent.

6. The composition of claim 5, wherein said carrier is a matrix.

7. The composition of claim 6, wherein said matrix is selected from the group consisting of fibrin, collagen, gelatin and agarose.

8. The composition of claim 5, wherein said carrier or diluent is selected from the group consisting of albumin, sterile water, polyethylene glycol and saline.

9. The composition of claim 5, wherein said composition includes an adjuvant.

10. A purified peptide consisting of an amino acid sequence selected from the group consisting of LVLDPK (SEQ ID NO:1), LVVDPK (SEQ ID NO:3), LVPDPK (SEQ ID NO:4), LVPDSK (SEQ ID NO:5), LVIDPK (SEQ ID NO:6) and VLDPK (SEQ ID NO:7).

11. A purified peptide consisting of the amino acid sequence KFHSHKDKLVLDPKSK (SEQ ID NO:2).

12. A purified chemotactic peptide which consists of the amino acid sequence VLDPK (SEQ ID NO:7).

13. A composition comprising the peptide of claim 3 in an amount suitable to effect chemotaxis and a pharmaceutically-acceptable carrier or diluent.

14. The composition of claim 13, wherein said carrier is a matrix.

15. The composition of claim 14, wherein said matrix is selected from the group consisting of fibrin, collagen, gelatin and agarose.

* * * * *

UNITED STATES PATENT AND TRADEMARK OFFICE
CERTIFICATE OF CORRECTION

PATENT NO. : 6,686,444 B2
DATED : February 3, 2004
INVENTOR(S) : Samy Ashkar

It is certified that error appears in the above-identified patent and that said Letters Patent is hereby corrected as shown below:

<u>Column 1,</u>
Line 7, please delete the word "from".
Line 8, at the beginning of the line before the word "the", please insert
-- under Grant No. IR29AR41046-01 awarded by --.

Signed and Sealed this

Twenty-second Day of June, 2004

JON W. DUDAS
*Acting Director of the United States Patent and Trademark Office*

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Osteopontin derived peptide

<400> SEQUENCE: 1

Leu Val Leu Asp Pro Lys
1               5

<210> SEQ ID NO 2
<211> LENGTH: 16
<212> TYPE: PRT
<213> ORGANISM: Artificial Sequence
<220> FEATURE:
<223> OTHER INFORMATION: Osteopontin Derived Peptide

<400> SEQUENCE: 2

Lys Phe His Ser His Lys Asp Lys Leu Val Leu Asp Pro Lys Ser Lys
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: Osteopontin Derived Peptide

<400> SEQUENCE: 3

Leu Val Val Asp Pro Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Osteopontin Derived Peptide

<400> SEQUENCE: 4

Leu Val Pro Asp Pro Lys
1               5

<210> SEQ ID NO 5
<211> LENGTH: 6
```

```
<212> TYPE: PRT
<213> ORGANISM: Artificial Sequence
<220> FEATURE:
<223> OTHER INFORMATION: Osteopontin Derived Peptide

<400> SEQUENCE: 5

Leu Val Pro Asp Ser Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Osteopontin Derived Peptide

<400> SEQUENCE: 6

Leu Val Ile Asp Pro Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Osteopontin Derived Peptide

<400> SEQUENCE: 7

Val Leu Asp Pro Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Osteopontin Derived Peptide

<400> SEQUENCE: 8

Gly Arg Gly Asp Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Osteopontin Derived Peptide

<400> SEQUENCE: 9

Leu Val Leu Ala Pro Lys
1               5
```